United States Patent
Eskaros et al.

(10) Patent No.: US 12,017,021 B2
(45) Date of Patent: Jun. 25, 2024

(54) NON-SHORTENING WRAPPED BALLOON

(71) Applicant: W. L. Gore & Associates, Inc., Newark, DE (US)

(72) Inventors: Sherif A. Eskaros, Elkton, MD (US); David R. King, Wilmington, DE (US); Joseph E. Korleski, Newark, DE (US); Lonzo C. McLaughlin, Landenberg, PA (US); Kenneth R. Newcomb, Middletown, DE (US); Peter J. Roeber, Oxford, PA (US); John Streeter, Flagstaff, AZ (US); Jeffrey C. Towler, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 989 days.

(21) Appl. No.: 16/919,843

(22) Filed: Jul. 2, 2020

(65) Prior Publication Data
US 2020/0330736 A1 Oct. 22, 2020

Related U.S. Application Data

(60) Continuation of application No. 14/078,225, filed on Nov. 12, 2013, now abandoned, which is a continuation of application No. 12/508,695, filed on Jul. 24, 2009, now Pat. No. 8,597,566, which is a
(Continued)

(51) Int. Cl.
*A61M 25/10* (2013.01)
*A61F 2/958* (2013.01)

(52) U.S. Cl.
CPC .............. *A61M 25/10* (2013.01); *A61F 2/958* (2013.01); *A61M 25/1029* (2013.01); *A61M 2025/1004* (2013.01); *A61M 25/1034* (2013.01); *A61M 2025/1075* (2013.01); *A61M 2025/1086* (2013.01)

(58) Field of Classification Search
CPC .............. A61M 25/1029; A61M 25/10; A61M 25/1034; A61M 2025/1075; A61M 2025/1086; A61M 2025/1004; A61F 2/958
See application file for complete search history.

(56) References Cited

U.S. PATENT DOCUMENTS

| | | |
|---|---|---|
| 1,690,995 A | 11/1928 | Pratt |
| 3,640,282 A | 2/1972 | Kamen et al. |
| 3,746,003 A | 7/1973 | Blake et al. |

(Continued)

FOREIGN PATENT DOCUMENTS

| | | | |
|---|---|---|---|
| EP | 0372088 A1 | 6/1990 | |
| EP | 0540858 A1 | 5/1993 | |

(Continued)

OTHER PUBLICATIONS

Dillon M. E, Silicone and Poly (tetrfluoroethylene) Interpenetrating Polymer Networks, 1994 American Chemical Society.
(Continued)

*Primary Examiner* — Monica A Huson (57) ABSTRACT

A non-shortening catheter balloon having a longitudinal axis and an inflatable balloon able to be affixed to a catheter shaft is provided. The balloon has an uninflated length which remains relatively unchanged upon inflation and is formed of least two helically oriented wrapped passes of balloon materials at a balanced force angle. Methods of making this balloon are also provided.

17 Claims, 5 Drawing Sheets

Related U.S. Application Data division of application No. 11/501,249, filed on Aug. 7, 2006, now abandoned.

(56) References Cited

U.S. PATENT DOCUMENTS

| | | |
|---|---|---|
| 3,953,566 A | 4/1976 | Gore |
| 4,003,382 A | 1/1977 | Dyke |
| 4,106,509 A | 8/1978 | McWhorter |
| 4,187,390 A | 2/1980 | Gore |
| 4,194,041 A | 3/1980 | Allen et al. |
| 4,279,245 A | 7/1981 | Takagi et al. |
| 4,280,500 A | 7/1981 | Ono |
| 4,304,010 A | 12/1981 | Mano |
| 4,327,736 A | 5/1982 | Inoue |
| 4,338,942 A | 7/1982 | Fogarty |
| 4,403,612 A | 9/1983 | Fogarty |
| 4,443,511 A | 4/1984 | Worden et al. |
| 4,490,421 A | 12/1984 | Levy |
| 4,573,966 A | 3/1986 | Weikl et al. |
| 4,596,839 A | 6/1986 | Peters |
| 4,608,984 A | 9/1986 | Fogarty |
| 4,613,544 A | 9/1986 | Burleigh |
| 4,619,641 A | 10/1986 | Schanzer |
| 4,637,396 A | 1/1987 | Cook |
| 4,650,466 A | 3/1987 | Luther |
| 4,702,252 A | 10/1987 | Brooks et al. |
| 4,706,670 A | 11/1987 | Andersen et al. |
| 4,713,070 A | 12/1987 | Mano |
| 4,737,219 A | 4/1988 | Taller et al. |
| 4,739,762 A | 4/1988 | Palmaz |
| 4,743,480 A | 5/1988 | Campbell et al. |
| 4,764,560 A | 8/1988 | Mitchell |
| 4,816,339 A | 3/1989 | Tu et al. |
| 4,819,751 A | 4/1989 | Shimada et al. |
| 4,832,688 A | 5/1989 | Sagae et al. |
| 4,896,669 A | 1/1990 | Bhate et al. |
| 4,946,464 A | 8/1990 | Pevsner |
| 4,955,899 A | 9/1990 | Della et al. |
| 5,041,047 A | 8/1991 | Casale |
| 5,061,276 A | 10/1991 | Tu et al. |
| 5,066,298 A | 11/1991 | Hess |
| 5,071,609 A | 12/1991 | Tu et al. |
| 5,087,244 A | 2/1992 | Wolinsky et al. |
| 5,100,429 A | 3/1992 | Sinofsky et al. |
| 5,108,370 A | 4/1992 | Walinsky |
| 5,112,304 A | 5/1992 | Barlow et al. |
| 5,116,318 A | 5/1992 | Hillstead |
| 5,137,512 A | 8/1992 | Burns et al. |
| 5,147,302 A | 9/1992 | Euteneuer et al. |
| 5,152,782 A | 10/1992 | Kowligi et al. |
| 5,171,297 A | 12/1992 | Barlow et al. |
| 5,192,296 A | 3/1993 | Bhate et al. |
| 5,195,970 A | 3/1993 | Gahara |
| 5,197,978 A | 3/1993 | Hess |
| 5,201,706 A | 4/1993 | Noguchi et al. |
| 5,211,654 A | 5/1993 | Kaltenbach |
| 5,213,576 A | 5/1993 | Abiuso et al. |
| 5,226,880 A | 7/1993 | Martin |
| 5,236,659 A | 8/1993 | Pinchuk et al. |
| 5,254,090 A | 10/1993 | Lombardi et al. |
| 5,256,143 A | 10/1993 | Miller et al. |
| 5,286,254 A | 2/1994 | Shapland et al. |
| 5,290,306 A | 3/1994 | Trotta et al. |
| 5,304,120 A | 4/1994 | Crandell et al. |
| 5,304,214 A | 4/1994 | Deford et al. |
| 5,304,340 A | 4/1994 | Downey |
| 5,308,356 A | 5/1994 | Blackshear et al. |
| 5,330,429 A | 7/1994 | Noguchi et al. |
| 5,338,299 A | 8/1994 | Barlow |
| 5,342,305 A | 8/1994 | Shonk |
| 5,342,348 A | 8/1994 | Kaplan |
| 5,348,538 A | 9/1994 | Wang et al. |
| 5,358,486 A | 10/1994 | Saab |
| 5,358,516 A | 10/1994 | Myers et al. |
| 5,366,442 A | 11/1994 | Wang et al. |
| 5,366,472 A | 11/1994 | Hillstead |
| 5,370,618 A | 12/1994 | Leonhardt |
| 5,403,340 A | 4/1995 | Wang et al. |
| 5,409,495 A | 4/1995 | Osborn |
| 5,415,636 A | 5/1995 | Forman |
| 5,425,710 A | 6/1995 | Khair et al. |
| 5,429,605 A | 7/1995 | Richling et al. |
| 5,456,661 A | 10/1995 | Narciso, Jr. |
| 5,458,568 A | 10/1995 | Racchini et al. |
| 5,458,605 A | 10/1995 | Klemm |
| 5,466,252 A | 11/1995 | Soukup et al. |
| 5,470,313 A | 11/1995 | Crocker et al. |
| 5,470,314 A | 11/1995 | Walinsky |
| 5,476,589 A | 12/1995 | Bacino |
| 5,478,320 A | 12/1995 | Trotta |
| 5,478,349 A | 12/1995 | Nicholas |
| 5,484,411 A | 1/1996 | Inderbitzen et al. |
| 5,490,839 A | 2/1996 | Wang et al. |
| 5,496,276 A | 3/1996 | Wang et al. |
| 5,498,238 A | 3/1996 | Shapland et al. |
| 5,499,973 A | 3/1996 | Saab |
| 5,499,980 A | 3/1996 | Euteneuer |
| 5,499,995 A | 3/1996 | Teirstein |
| 5,500,180 A | 3/1996 | Anderson et al. |
| 5,500,181 A | 3/1996 | Wang et al. |
| 5,512,051 A | 4/1996 | Wang et al. |
| 5,519,172 A | 5/1996 | Spencer et al. |
| 5,527,282 A | 6/1996 | Segal |
| 5,529,820 A | 6/1996 | Nomi et al. |
| 5,571,089 A | 11/1996 | Crocker |
| 5,609,605 A | 3/1997 | Marshall et al. |
| 5,613,979 A | 3/1997 | Trotta et al. |
| 5,620,649 A | 4/1997 | Trotta |
| 5,641,373 A | 6/1997 | Shannon et al. |
| 5,645,560 A | 7/1997 | Crocker et al. |
| 5,647,848 A | 7/1997 | Jorgensen |
| 5,681,522 A | 10/1997 | Roychowdhury |
| 5,695,469 A | 12/1997 | Segal |
| 5,716,340 A | 2/1998 | Schweich et al. |
| 5,716,396 A | 2/1998 | Williams, Jr. |
| 5,752,934 A | 5/1998 | Campbell et al. |
| 5,766,201 A | 6/1998 | Ravenscroft et al. |
| 5,797,877 A | 8/1998 | Hamilton et al. |
| 5,807,327 A | 9/1998 | Green et al. |
| 5,843,116 A | 12/1998 | Crocker et al. |
| 5,868,704 A | 2/1999 | Campbell et al. |
| 5,868,708 A | 2/1999 | Hart et al. |
| 5,893,840 A | 4/1999 | Hull et al. |
| 5,908,406 A | 6/1999 | Ostapchenko et al. |
| 5,931,851 A | 8/1999 | Morales |
| 5,944,734 A | 8/1999 | Hermann et al. |
| 5,948,345 A | 9/1999 | Patel et al. |
| 5,951,941 A | 9/1999 | Wang et al. |
| 5,954,745 A | 9/1999 | Gertler et al. |
| 5,972,441 A | 10/1999 | Campbell et al. |
| 6,010,480 A | 1/2000 | Abele et al. |
| 6,013,092 A | 1/2000 | Dehdashtian et al. |
| 6,027,779 A | 2/2000 | Campbell et al. |
| 6,048,356 A | 4/2000 | Ravenscroft et al. |
| 6,063,092 A | 5/2000 | Shin |
| 6,074,381 A | 6/2000 | Dinh et al. |
| 6,120,477 A | 9/2000 | Campbell et al. |
| 6,132,824 A | 10/2000 | Hamlin |
| 6,156,254 A | 12/2000 | Andrews et al. |
| 6,234,995 B1 | 5/2001 | Peacock, III |
| 6,287,290 B1 | 9/2001 | Perkins et al. |
| 6,287,314 B1 | 9/2001 | Lee et al. |
| 6,319,249 B1 | 11/2001 | Toellner |
| 6,319,259 B1 | 11/2001 | Lee et al. |
| 6,319,529 B1 | 11/2001 | Thompson |
| 6,336,937 B1 | 1/2002 | Vonesh et al. |
| 6,375,637 B1 | 4/2002 | Campbell et al. |
| 6,428,506 B1 | 8/2002 | Simhambhatla et al. |
| 6,482,348 B1 | 11/2002 | Wang et al. |
| 6,488,688 B2 | 12/2002 | Lim et al. |
| 6,572,813 B1 | 6/2003 | Zhang et al. |
| 6,602,224 B1 | 8/2003 | Simhambhatla |
| 6,663,646 B1 | 12/2003 | Shah |
| 6,746,425 B1 | 6/2004 | Beckham |

(56) References Cited

U.S. PATENT DOCUMENTS

| | | |
|---|---|---|
| 6,756,094 B1 | 6/2004 | Wang et al. |
| 6,841,029 B2 | 1/2005 | Lim |
| 6,887,227 B1 | 5/2005 | Barbut |
| 6,890,395 B2 | 5/2005 | Simhambhatla |
| 6,905,743 B1 | 6/2005 | Chen et al. |
| 6,923,827 B2 | 8/2005 | Campbell et al. |
| 6,939,593 B2 | 9/2005 | Wang |
| 6,946,173 B2 | 9/2005 | Lim et al. |
| 6,977,103 B2 | 12/2005 | Chen et al. |
| 7,052,507 B2 | 5/2006 | Wakuda et al. |
| 7,195,638 B1 | 3/2007 | Sridharan |
| 7,279,208 B1 | 10/2007 | Goffena et al. |
| 7,306,729 B2 | 12/2007 | Bacino et al. |
| 7,309,324 B2 | 12/2007 | Hayes et al. |
| 7,625,337 B2 | 12/2009 | Campbell et al. |
| 7,785,290 B2 | 8/2010 | Alpini et al. |
| 7,892,201 B1 | 2/2011 | Laguna et al. |
| 8,192,477 B2 | 6/2012 | Mertens et al. |
| 8,597,566 B2 | 12/2013 | Eskaros et al. |
| 2001/0008970 A1 | 7/2001 | Ravenscroft et al. |
| 2001/0043998 A1 | 11/2001 | Chen et al. |
| 2002/0087165 A1 | 7/2002 | Lee et al. |
| 2002/0161388 A1 | 10/2002 | Samuels et al. |
| 2002/0163104 A1 | 11/2002 | Motsenbocker et al. |
| 2003/0074016 A1 | 4/2003 | Campbell et al. |
| 2003/0083687 A1 | 5/2003 | Pallazza |
| 2003/0088209 A1 | 5/2003 | Chiu et al. |
| 2003/0130716 A1 | 7/2003 | Weber et al. |
| 2003/0211258 A1 | 11/2003 | Sridharan et al. |
| 2004/0002750 A1 | 1/2004 | Majercak |
| 2004/0015183 A1 | 1/2004 | Lim et al. |
| 2004/0082965 A1 | 4/2004 | Beckham |
| 2004/0143287 A1 | 7/2004 | Konstantino et al. |
| 2004/0191442 A1 | 9/2004 | Lim |
| 2004/0199202 A1 | 10/2004 | Dubrul et al. |
| 2004/0230309 A1 | 11/2004 | Dimauro et al. |
| 2004/0254625 A1 | 12/2004 | Stephens et al. |
| 2005/0015048 A1 | 1/2005 | Chiu et al. |
| 2005/0038503 A1 | 2/2005 | Greenhalgh et al. |
| 2005/0059957 A1 | 3/2005 | Campbell et al. |
| 2005/0267409 A1 | 12/2005 | Shkolnik |
| 2005/0273152 A1 | 12/2005 | Campbell et al. |
| 2006/0041091 A1 | 2/2006 | Chang et al. |
| 2006/0085024 A1 | 4/2006 | Pepper et al. |
| 2006/0136032 A1 | 6/2006 | Legarda et al. |
| 2006/0161102 A1 | 7/2006 | Newcomb et al. |
| 2006/0271091 A1 | 11/2006 | Campbell et al. |
| 2007/0055301 A1 | 3/2007 | Campbell et al. |
| 2007/0061000 A1 | 3/2007 | Campbell et al. |
| 2007/0219489 A1 | 9/2007 | Johnson et al. |
| 2008/0097301 A1 | 4/2008 | Alpini et al. |
| 2008/0097374 A1 | 4/2008 | Korleski et al. |
| 2008/0125711 A1 | 5/2008 | Alpini et al. |
| 2008/0140173 A1 | 6/2008 | Eskaros et al. |
| 2008/0183132 A1 | 7/2008 | Davies et al. |
| 2008/0255507 A1 | 10/2008 | Mushtaha |
| 2008/0257155 A1 | 10/2008 | Bacino et al. |
| 2008/0312730 A1 | 12/2008 | Campbell et al. |
| 2009/0032470 A1 | 2/2009 | Bacino et al. |
| 2009/0038752 A1 | 2/2009 | Weng et al. |
| 2009/0053103 A1 | 2/2009 | Mortimer et al. |
| 2009/0283206 A1 | 11/2009 | Eskaros et al. |
| 2010/0049123 A1 | 2/2010 | Alpini et al. |
| 2010/0179581 A1 | 7/2010 | Beckham |
| 2010/0262178 A1 | 10/2010 | Alpini et al. |
| 2011/0093001 A1 | 4/2011 | Meens |
| 2014/0088683 A1 | 3/2014 | Eskaros et al. |

FOREIGN PATENT DOCUMENTS

| | | |
|---|---|---|
| EP | 0628586 A1 | 12/1994 |
| EP | 0737488 A1 | 10/1996 |
| EP | 0769307 A2 | 4/1997 |
| EP | 0829269 A1 | 3/1998 |
| GB | 1566674 A | 5/1980 |
| NL | 1008178 C2 | 8/1999 |
| WO | 90/14054 A1 | 11/1990 |
| WO | 94/02185 A1 | 2/1994 |
| WO | 95/05555 A1 | 2/1995 |
| WO | 95/09667 A1 | 4/1995 |
| WO | 95/17920 A1 | 7/1995 |
| WO | 96/14895 A1 | 5/1996 |
| WO | 96/40350 A1 | 12/1996 |
| WO | 97/02791 A1 | 1/1997 |
| WO | 97/40877 A1 | 11/1997 |
| WO | 02/68011 A1 | 9/2002 |
| WO | 03/00307 A1 | 1/2003 |
| WO | 2008/021002 A1 | 2/2008 |
| WO | 2008/021003 A1 | 2/2008 |
| WO | 2008/021006 A2 | 2/2008 |
| WO | 2008/021013 A1 | 2/2008 |

OTHER PUBLICATIONS

International Preliminary Report on Patentability received for PCT Patent Application No. PCT/US2007/017218, dated Feb. 10, 2009, 13 pages.

International Search Report and Written Opinion received for PCT Patent Application No. PCT/US2007/017218, dated Jul. 3, 2008, 17 pages.

NON-SHORTENING WRAPPED BALLOON

CROSS-REFERENCE TO RELATED APPLICATION

This application is a continuation of U.S. patent application Ser. No. 14/078,225, filed Nov. 12, 2013, which is a continuation of U.S. application Ser. No. 12/508,695, filed Jul. 24, 2009, now U.S. Pat. No. 8,597,566, issued Dec. 3, 2013, which is a divisional of U.S. application Ser. No. 11/501,249, filed Aug. 7, 2006, now abandoned, all of which are incorporated herein by reference in their entireties for all purposes.

BACKGROUND OF THE INVENTION

The present invention relates to balloon catheters and, more particularly, to a non-shortening wrapped balloon configured to expand with essential radial symmetry to a predetermined diameter upon application of a predetermined pressure thereto.

Balloon catheters are well known in the art. Such catheters are employed in a variety of medical procedures, including dilation of narrowed blood vessels, placement of stents and other implants, and temporary occlusion of blood vessels.

In a typical application, the balloon is advanced to the desired location in the vascular system. The balloon is then pressure-expanded in accordance with a medical procedure. Thereafter, the pressure is removed from the balloon, allowing the balloon to contract and permit removal of the catheter. The balloon must be formed of a material which has a low profile to allow entry through a vessel, yet is readily pressure-expanded and able to contract upon removal of the inflation pressure.

Procedures such as these are generally considered minimally invasive, and are often performed in a manner which minimizes disruption to the patient's body. As a result, catheters are often inserted from a location remote from the region to be treated. However, previous wrapped balloons have suffered from problems such as overexpansion during inflation and shortening of the balloon due to inflation resulting in unreliable placement of the balloon in a vessel. This is particularly concerning when large diameter balloon are employed in medical procedures because the maximum hoop stress of the inflated balloon material can more easily be exceeded causing the balloon to rupture or burst.

Previous attempts to compensate for overexpansion have been made.

However, only the present invention provides a non-shortening balloon that expands to a maximum diameter in an essentially radial symmetric fashion. While an advantage of a low angle wrapped balloon is that the wrap is accomplished at the deflated diameter making mounting to a catheter shaft possible. The balloon then inflates to a larger diameter in use at which time the wrap angle rotates to the neutral angle. A typical low angle wrapped balloon will foreshorten as it is expanded. Compensation for foreshortening by means of accordion-scrunching-length-storage is limited in that the longitudinal folds push out and then the angle moves to the neutral angle thus the foreshortening is not eliminated during inflation. The devices and methods of the present invention minimize foreshortening while maintaining an essentially radial inflating balloon, and allow the balloon to be mounted on a smaller diameter catheter shaft. The present invention solves the clinical issues of accurate placement of a balloon or stent due to foreshortening of traditional wrapped balloons. The present invention also prevents undue trauma on vessel endothelial layers and possibility of plaque fragmentation caused by inflation movement of asymmetric inflating balloons.

SUMMARY OF THE INVENTION

The present invention is a balloon catheter comprising a catheter shaft having a longitudinal axis and an inflatable balloon affixed to said shaft, said balloon having an uninflated length which remains relatively unchanged upon inflation and comprising at least two helically oriented layers oriented at a balanced force angle.

A non-shortening wrapped catheter balloon having a longitudinal axis, comprising a first balloon material layer fused to a second balloon material layer is provided, wherein the first balloon material is oriented at an angle of less than or equal to about 55 degrees and the second balloon material is oriented at an opposing angle of less than or equal to about 55 degrees with respect to the longitudinal axis. These opposing angle layers create a balloon preform.

A method of creating a non-shortening catheter balloon with increased burst pressures is provided, said balloon comprising: wrapping a mandrel with an anisotropic film at a low angle to form a balloon preform; removing the mandrel; exposing the balloon preform to internal pressure at a temperature to soften or a melt point for the film or imbibing material; and inflating the balloon preform into a balloon as it is continued to be exposed to said internal pressure at an increased temperature.

A method of creating a non-shortening catheter balloon with increased burst pressures is provided comprising: wrapping a mandrel with an anisotropic film at a low angle to form a balloon preform; exposing the balloon preform to internal pressure at temperatures below melting point of the film; inflating the balloon as it is continued to be exposed to said internal pressure and constant temperature; and wrapping the inflated balloon with an overwrap at an angle between 54 and 90 degrees to form a high pressure catheter balloon that is retractable.

A method of creating a non-shortening catheter balloon with increased burst pressures is provided comprising: wrapping a mandrel with an anisotropic film at a low angle to form a balloon preform; removing the mandrel; exposing the balloon preform to internal pressure at temperatures above ambient to soften or melt the film, inflating the balloon as it is continued to be exposed to said internal pressure and constant temperature; and wrapping the inflated balloon helically with an anisotropic material at a high angle of between 54 and 90 degrees to form a high pressure catheter balloon.

DETAILED DESCRIPTION OF THE INVENTION

The balloon catheter of the present invention in its simplest form comprises a catheter shaft having a longitudinal axis and an inflatable balloon affixed thereto. The balloon is comprised of at least two passes. An individual pass is comprised of one or more layers of material which are laid at a similar angle in relation to the longitudinal axis of the balloon. A layer is considered to be one thickness of balloon material which may be wrapped, folded, laid or weaved over, around, beside or under another thickness. A longitudinal pass comprises a distinctive layer or series of layers of material which are wound to form a region or area distinct from surrounding or adjoining parts. For instance a pass may comprise multiple layers of balloon material wrapped at a 90 degree angle relative to the longitudinal axis. This exemplary pass may then be flanked by layers of balloon material wrapped at dissimilar angles in relation to the longitudinal axis, thus defining the boundary of the pass.

A pass of balloon material may be oriented helically, radially or longitudinally. By layers of balloon material it is meant to include pieces, threads, layers, filaments, membranes, or sheets of suitable balloon material. In helically oriented layers, the material is oriented so to form a balanced force angle in relation to each other upon inflation. The layers may further be wound upon themselves in subsequent passes. A balanced force balloon of the present invention is a balloon possessing a combination of passes to create the strength to balance the radial force exerted by inflation pressures on the balloon vessel with respect to the longitudinal forces exerted by inflation so that the balloon inflates to its desired diameter without any longitudinal movement. One method of achieving a balanced-force-angle balloon is to orient the helical layers to approach the geometrically derived neutral angle value of 54.7 degrees. This neutral angle is derived from balancing the forces in a thin walled pressure vessel where: 2×Axial stress=Hoop stress. The inflatable balloon of the present invention exhibits both essentially radial symmetry upon inflation and non-foreshortening. Radial symmetry is exhibited upon inflation as the movement of the balloon material away from the center point of the lumen in a direct radial fashion so that the balloon maintains a relatively radial outward movement which resists twisting of the balloon surface as the balloon inflates. By non-foreshortening it is meant that the length of the balloon does not change by more than ten percent upon inflation to a rated burst pressure. In preferred applications, the balloon does not change length by more than 5 percent upon inflation to a rated burst pressure. In further preferred applications, the balloon does not change length by more than 2 percent upon inflation to a rated burst pressure. A radial symmetry upon inflation allows the balloon to exhibit an equal hydrostatic force on a vessel wall in clinical use. When used with a stent or stent graft, an equal hydrostatic force allows uniform deployment capability. Uniform stent deployment is preferred so that less trauma is inflicted on the vessels and more efficient vessel scaffolding is achieved, as compared to other types of deployment.

Figure 1:
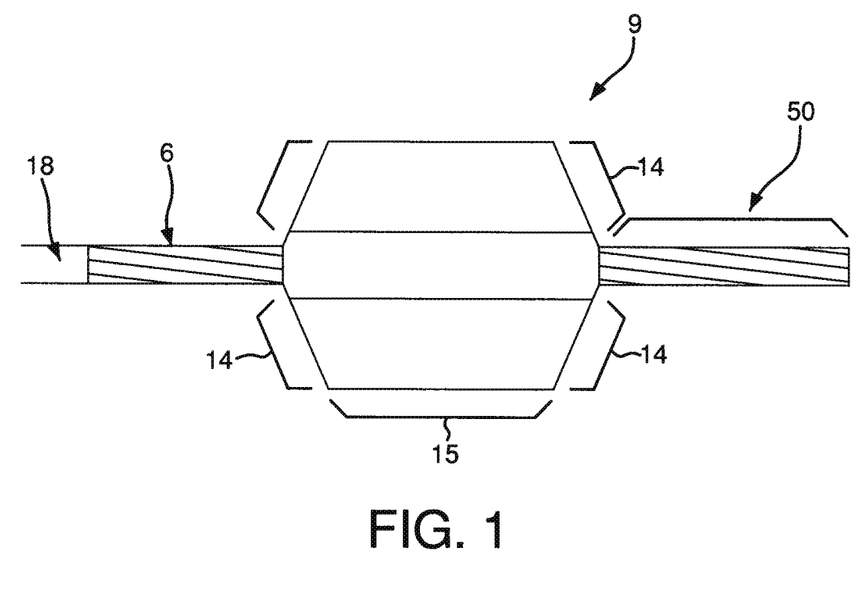
FIG. 1 shows a schematic of a wrapped balloon of the present invention.
Figure 2:
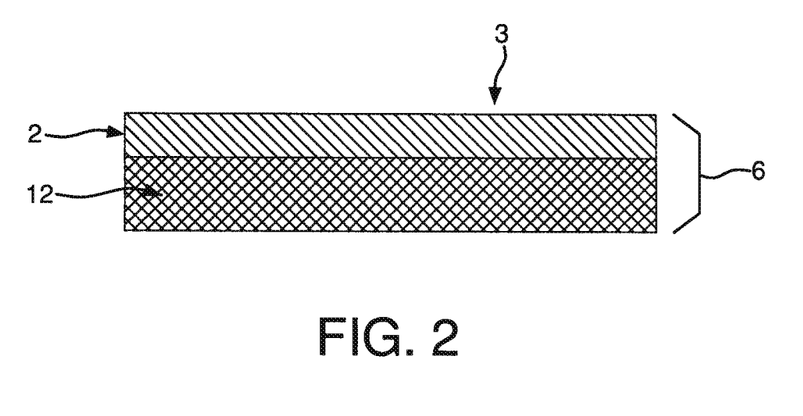
FIG. 2 shows a balloon material with a single side coating.

In one embodiment as shown in FIG. 1, an inflatable device of the present invention comprises a catheter shaft 18 having a longitudinal axis and an inflatable balloon 9 affixed to the shaft, the balloon has an un-inflated length which remains relatively unchanged as the balloon is inflated and comprises at least two helical wrap passes of a balloon material 6. The at least two passes may be fused together. The balloon has a working length 15, shoulders 14, and wrapped balloon material 6 on the legs 50 of the balloon. As shown in FIG. 2, the balloon material 6 comprises a porous reinforcing polymer 1 and a polymer coating 2. The polymer coating is imbibed into the porous reinforcing polymer to form a continuous polymer layer 12. The porous reinforcing polymer may comprise a fibrous reinforcement, a porous membrane such as, a polyolefin, a fluoropolymer, a discontinuous phase of a polymer, or an oriented microporous reinforcement, such as ePTFE. In the present invention it is desirable to use expanded PTFE (ePTFE) as a porous reinforcing polymer, allowing the balloon material to realize a matrix tensile value in one direction greater than 690 megapascals; or preferably greater than 960 megapascals; more preferably greater than 1,200 megapascals.

The oriented microporous reinforcement may be a fluoropolymer, a polyamide, a polyurethane, a polyester, a PEEK, a reinforced polymer, or any other suitable materials or combination of materials. The polymer coating 2 is imbibed throughout the porous reinforcing polymer and may comprise a fluoropolymer, an elastomer, a urethane, a silicone, a styrene block copolymer, a fluoro-elastomer, a bioresorbable material or any other suitable polymer. As further shown in FIG. 1, the balloon comprises a working length 15 between two shoulders 14 of the balloon. In a preferred embodiment, the balloon comprises at least one hoop pass wrapped over the working length and a shoulder pass having a thickness ratio between the hoop layer and the shoulder layer of 2:1. The balloon material layers forming the individual passes may be heated or set in position relative to each other after each pass.

Typical low angle wrapped balloons tend to foreshorten as they inflate and the wrap angle rotates towards the neutral angle. Less obvious is that the wrap layers also strain perpendicular to the wrap angle during the rotation caused by inflation. The growth in the wrap layer width follows this geometrically derived equation: $(Width_F = Width_I \times (\cos \theta_F / \cos \theta_I)^2 \times (\tan \theta_F / \tan \theta_I)$ where F is final and I is initial, and $\theta$ is the angle of the helical wrap relative to the longitudinal axis of the balloon. This strain can exceed 500 percent in some balloons depending on the deflated to inflated ratio. Highly anisotropic materials are necessary to allow this perpendicular stain. The wrap layers when configured in accordance with the present invention, reset a low angle wrapped balloon at or near a balanced force angle which prevents the layers from incurring transverse strain in subsequent balloon inflations. Additionally, the balloon exhibits essentially radial symmetry upon inflation. The balloon is wrapped by winding layers at opposing directions to one another until a desired thickness is obtained. The balloon material passes may be comprised of the same materials or different materials. While the thickness of the materials may vary, for vascular use it is advantageous to use balloon material that is about 4-6 micrometers thick.

Figure 3:
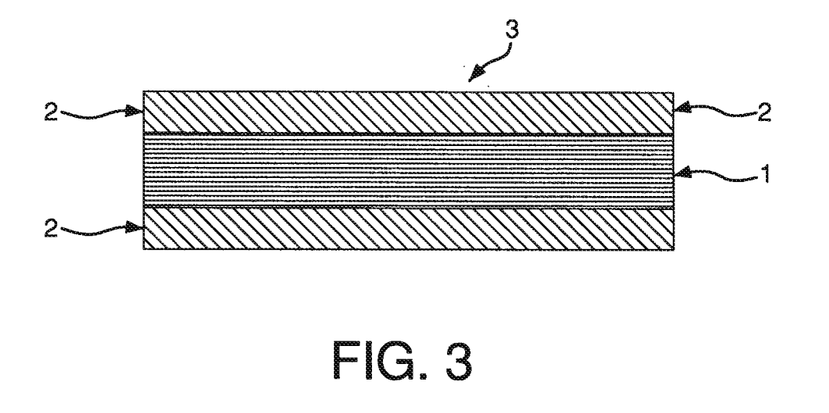
FIG. 3 shows a balloon material with a double sided coating.

As shown in FIGS. 2 and 3, a balloon material comprising a polymer layer 2 is coated on the porous reinforcement polymer 1 allowing the polymer coating to fill the void spaces of the porous reinforcement polymer 1. The polymer layer 2 may desirably fill the void spaces in the porous reinforcement polymer 1 to form a filled polymer layer 12.

The polymer layer 2 may be formed on one side of the porous reinforcing polymer 1 (FIG. 2) or on both sides of the porous reinforcing polymer 1 (FIG. 3). The composite film 3 may further comprise a filler. The filler may provide benefits such as radio opaque marking or therapeutic value. The balloon material may be cut into more narrow widths if necessary to form wrapping layers used in the balloon. An anisotropic material is used as a wrap layer in balloon passes consisting of wrap layer angles of less than about 55 degrees. However, if an overwrap pass is employed it may comprise isotropic or anisotropic material depending on desired applications.

The composite film 3 of the present invention comprises a porous reinforcing layer and a continuous polymer layer as depicted in FIGS. 2 and 3. The porous reinforcing polymer layer 1 is preferably a thin strong porous membrane that can be made in sheet form. The porous reinforcing polymer can be selected from a group of polymers including but not limited to: olefin, PEEK, polyamide, polyurethane, polyester, polyethylene, and polytetrafluoroethylene. In a preferred embodiment the porous reinforcing polymer is expanded polytetrafluoroethylene (ePTFE) made in accordance with the general teachings of U.S. Pat. No. 5,476,589 and U.S. patent application Ser. No. 11/334,243. In this preferred embodiment, the ePTFE membrane is anisotropic such that it is highly oriented in the one direction. An ePTFE membrane with a matrix tensile value (matrix tensile stress or MTS) in one direction of greater than 690 megapascals is preferred, and greater than 960 megapascals is even more preferred, and greater than 1,200 megapascals is most preferred. The exceptionally high MTS of ePTFE membrane allows the composite material to withstand very high hoop stress in the inflated balloon configuration. In addition, the high matrix tensile value of the ePTFE membrane makes it possible for very thin layers to be used which reduces the deflated balloon profile. A small profile is necessary for the balloon to be able to be positioned in small arteries or veins or orifices. In order for balloons to be positioned in some areas of the body, the balloon catheter must be able to move through a small bend radius, and a thinner walled tube is typically much more supple and capable of bending in this manner without creasing or causing damage to the wall of the vessel.

The continuous polymer layer 2 of the present invention is coated onto at least one side of the porous reinforcing polymer 1 as depicted in FIGS. 2 & 3. The continuous polymer layer is preferably an elastomer, such as but not limited to, aromatic and aliphatic polyurethanes including copolymers, styrene block copolymers, silicones, preferably thermoplastic silicones, fluoro-silicones, fluoroelastomer, THV and latex. In one embodiment of the present invention, the continuous polymer layer 2 is coated onto only one side of the porous reinforcing polymer 1, as shown in FIG. 2. As depicted in FIG. 3, the continuous polymer layer 2 is coated onto both sides of the porous reinforcing polymer 1. In one aspect, the continuous polymer layer 2 is imbibed into the porous reinforcing polymer 1 and the imbibed polymer 2 fills the pores of the porous reinforcing polymer 1 to form a composite 12.

The continuous polymer layer can be applied to the porous reinforcing polymer through any number of conventional methods including but not limited to, lamination, transfer roll coating, wire-wound bar coating, reverse roll coating, and solution coating or solution imbibing. In a preferred embodiment, the continuous polymer layer is solution imbibed into the porous reinforcing polymer. In this embodiment, the continuous polymer layer polymer is dissolved in a suitable solvent and coated onto and throughout the porous reinforcing polymer using a wire-wound rod process. The coated porous reinforcing polymer is then passed through a solvent oven and the solvent is removed leaving a continuous polymer layer coated onto and throughout the porous reinforcing polymer. In some cases, such as when silicone is used as the continuous polymer layer, the coated porous reinforcing polymer may not require the removal of solvent. In another embodiment, the continuous polymer layer is coated onto at least one side of the porous reinforcing polymer and maintained in a "green" state where it can be subsequently cured. For example, an ultraviolet light (UV) curable urethane may be used as the continuous polymer layer and coated onto the porous reinforcing polymer. The composite film comprising the porous reinforcing polymer and the UV curable urethane continuous polymer layer can then be wrapped to form at least one layer of the balloon and subsequently exposed to UV light and cured.

In another aspect of this invention, the helically wrapped passes of balloon material are bonded to each other. A preferred bonding technique is heat although other types of bonding may be used. The balloon material is then annealed in the inflated state through the application of heat to reset the low angle wrap balloon perform at or near a balanced force angle.

Figure 4:
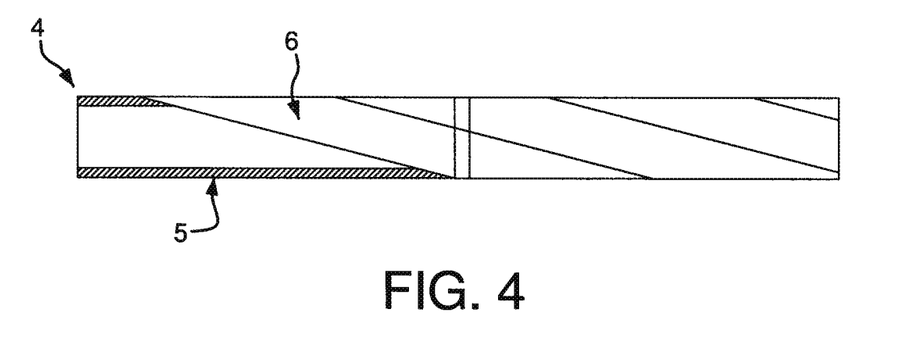
FIG. 4 shows a schematic of a partially wrapped balloon.
Figure 5:
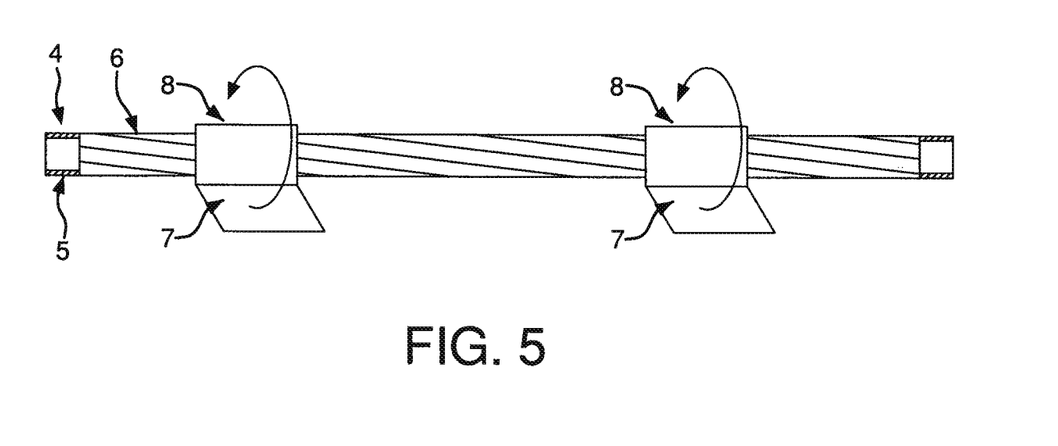
FIG. 5 shows a cross section of wrapped balloon on a core.

As shown in FIGS. 4 and 5, the first balloon material 6 may be wrapped around a core wire 4. The core wire 4 may be coated with a release agent 5, such as an FEP coating or other suitable agent. The helical wrap layers are first laid across the longitudinal axis in one direction or pass. A second pass lays another helical wrap layer in the opposing direction. Both passes 6 are oriented at an angle of less than or equal to about 55 degrees with respect to the longitudinal axis but in opposing directions. FIG. 5 shows that non-distensible layers 7 may be present to form non-distensible regions 8. The helically wrap layers of a first balloon material pass may be bonded to a second balloon material pass through the application of heat, or another suitable bonding technique. These balloon preforms are wrapped at a low angle to facilitate sealing to a catheter shaft. The distensible region of the preform is then inflated and the helical wrapped layers of the first material are reset at a balanced force angle through heating, solvating, annealing, or through a second material added while in the inflated state. The second material may be comprised of the same or different materials as the first material.

Figure 6:
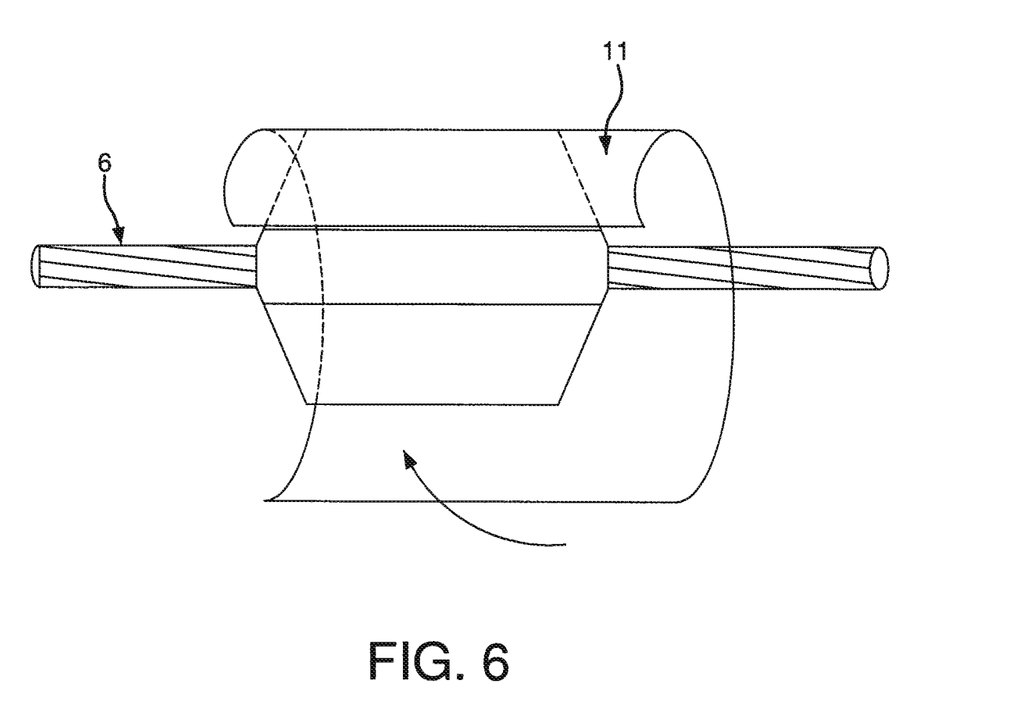
FIG. 6 shows a cross section of wrapped balloon on a core with a cigarette wrapped second balloon material pass.
Figure 8:
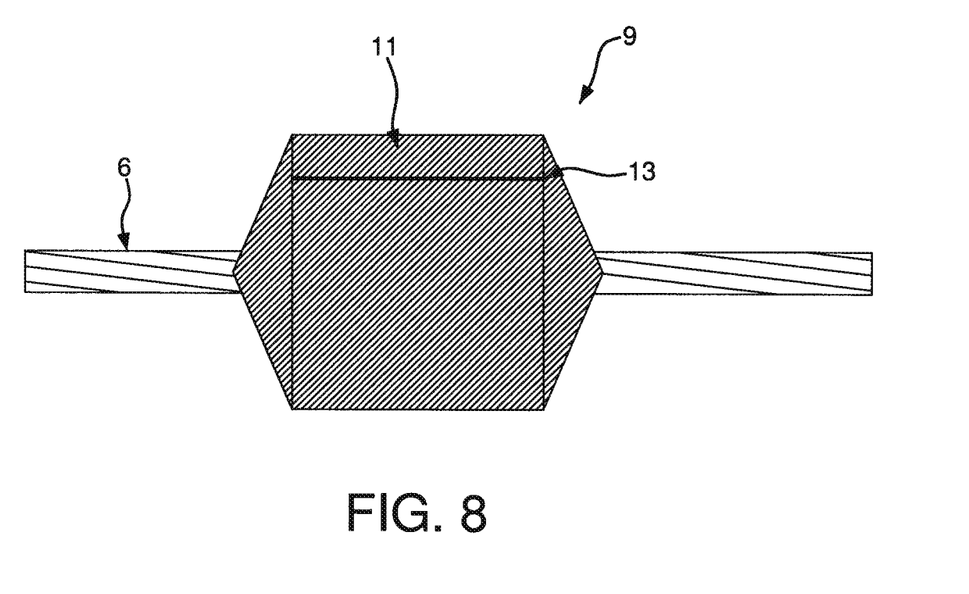
FIG. 8 shows a cross section of wrapped balloon on a core with an overlapped cigarette wrap of second balloon material pass.

In one preferred embodiment as shown in FIGS. 6 and 8, a balloon material 6 is wrapped into at least two passes to form a balloon preform and then is fused and inflated to form the shape of a catheter balloon. The balloon material 6 is then held at balanced force angle by second balloon material layer 11 which is cigarette wrapped around the first balloon material at an angle greater than 54 degrees relative to the longitudinal axis of the catheter balloon. It is preferred that two ends of the second balloon material overlap to form a longitudinally oriented seam 13, as shown in FIG. 8.

Figure 7:
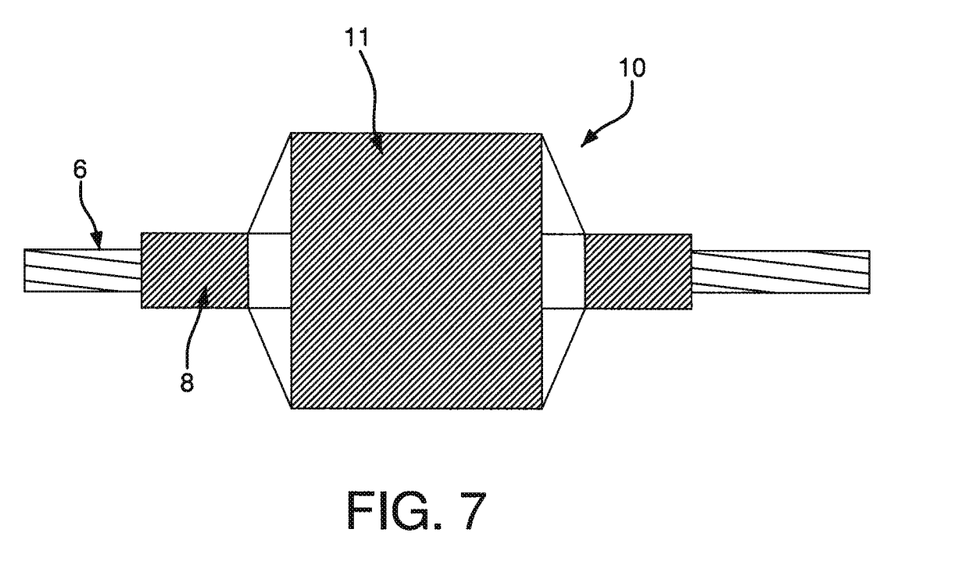
FIG. 7 shows a cross section of wrapped balloon on a core with a cigarette wrapped second balloon material pass and non-distending regions.
Figure 9:
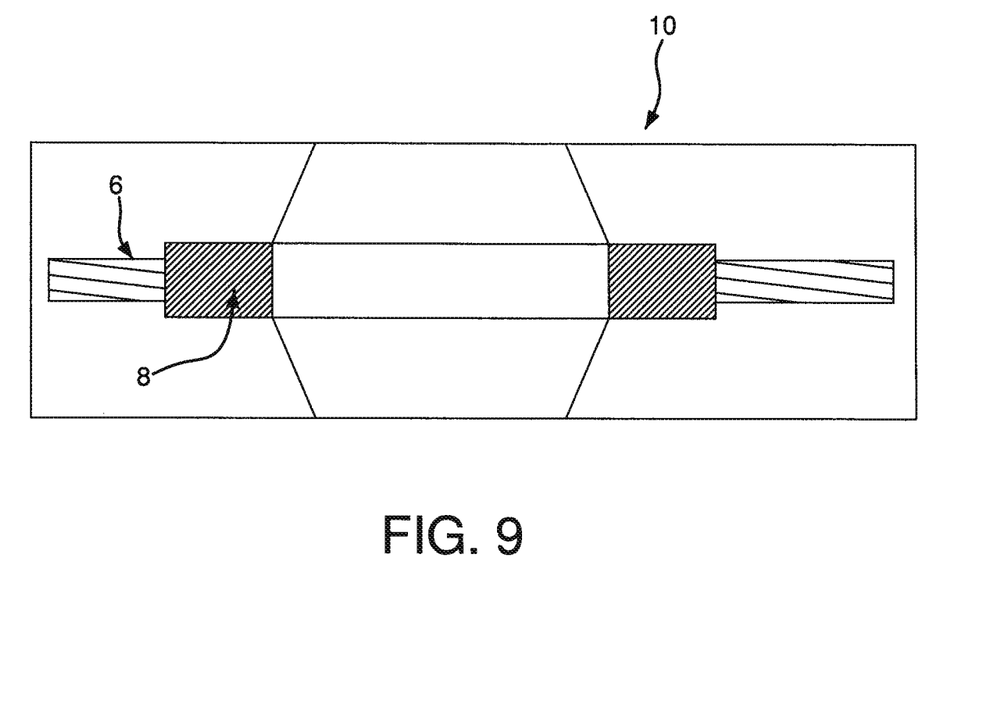
FIG. 9 shows a mold-shaped catheter balloon with non-distensible regions.

In another preferred embodiment as shown in FIGS. 7 and 9, a balloon material 6 is wrapped into a low angle balloon preform. The balloon is inflated in an inflation mold 10 as shown in FIG. 9. The inflation mold 10 is of a desired shape to form a catheter balloon which is then held at balanced force angle by second pass of balloon material 11 that is helically wrapped around the molded catheter balloon at an angle greater than 54 degrees but not greater than 90 degrees relative to the longitudinal axis of the catheter balloon. A non-distensible region 8 may be included in the balloon as shown in FIGS. 5, 7, and 9. The non-distending regions 8 are focal regions which are more resistant to radial dilatation allowing for reduction of load or sealing of an inflated balloon to an underlying catheter shaft. A non-distending region 8 comprises a plurality of non-distensible layers 7 which wind around the balloon material 6 and overlap to form an angle of between 0 degrees to 90 degrees relative to the longitudinal axis of the balloon. The non-distending regions 8 are incorporated or integrated into the surface of the balloon wall, into the balloon wall, or under the outer most surface of the balloon wall. The non-distending regions 8 are in direct continuity with the balloon wall and are virtually indistinguishable in form from the balloon wall in an un-inflated state.

The second balloon material 11 may be isotropic, having a relatively equal strength in all directions or anisotropic having an oriented longitudinal strength.

The balloons of the present invention expand from a low-profile delivery configuration to an inflated configuration in a uniform concentric manner over substantially its entire working length. The present invention is applicable for use with non-compliant or semi-compliant balloons.

In another embodiment, the inventive balloon comprises a balloon material 6 wrapped into a low angle preform and inflated to form the shape of a catheter balloon which is then further wrapped and held at a balanced force angle by a pass or passes of second balloon material oriented at an angle greater than 54 degrees with respect to the longitudinal balloon axis. It is desirable to orient the second balloon material helically in direction of the maximum hoop stress to create a high pressure balloon. It is desirable to use ePTFE as the porous reinforcing polymer in the composite film of a balloon layer to achieve a maximum hoop stress of the helically wrapped layers in greater than 400 megapascals. Even more desirable is achieving a maximum hoop stress of the helically wrapped layers in greater than 600 megapascals.

Figure 10:
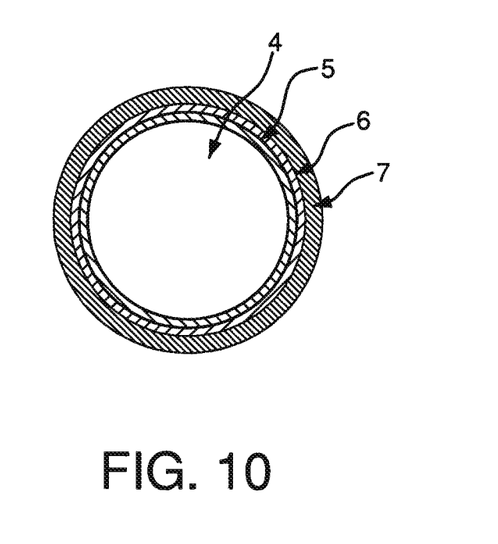
FIG. 10 shows a cross-section view of a wrapped balloon with non-distensible regions.

The balloon materials may comprise a filler if desired to alleviate leakage of the membrane or to deliver therapeutic agents. The filler may be radio opaque or provide therapeutic value. The balloon may further comprise one or more integral non-distending regions, as described above. An integral non-distending region may be located between two or more layers of balloon material or located on the surface of a balloon material 6 to form a non-distending region 8 (see FIGS. 5 and 10). FIG. 10 shows a core wire 4 with a release agent 5, a balloon material 6 and a surface mounted non-distensible layer 7 forming a seal. The non-distending region, as depicted in FIG. 5, is formed by changing the wrapping angle of the balloon material layers to create a build up of non-distending passes. The non-distending passes overlap each other either wholly or partially to form one or more non-distending regions 8 on the wrapped distensible balloon. The non-distending regions 8 are significantly less compliant under distention force than a distensible main body of the balloon. The non-distending region may comprise the same material as a distensible balloon material 6 or a different material. It is preferable that the non-distending region 8 undergoes little or no change in radial diameter upon introduction of distention force.

The present invention further contemplates that a balloon catheter comprising a catheter shaft with a longitudinal axis and an inflatable balloon of the present invention affixed to the shaft. A catheter balloon of the present invention may be used in conjunction with a stent. When at least the second balloon material exhibits a low modulus, the balloon material is able to pillow into the stent interstices. Thus, the pillow areas which fill in the interstices of a stent provide stent embedment prior to stent delivery. In this manner the stent is embedded without the use of heat, and without balloon inflation.

A method of creating a non-shortening catheter balloon with increased burst pressures is also provided, comprising wrapping a wire core with a plurality of balloon material layers or pieces at a angle of between 3 and 54 degrees relative to the longitudinal axis of the balloon to form a balloon preform; exposing the plurality of balloon material layers to heat to bond them together; removing the core; and then further exposing the balloon preform to internal pressure at a reflow temperature. The reflow temperature is the temperature to soften or a melt point for the film or imbibing material; and inflating the balloon preform into a balloon as it is continued to be exposed to said internal pressure at an increased temperature. At this point if desired the balloon may be wrapped with a second balloon material layer at a high angle of between 54 and 90 degrees. The second balloon material may be fused to the inflated balloon by the application of heat or other desired bonding technique. The balloon is then removed from exposure to reflow temperature and internal pressure to create a non-shortening balloon. When a second balloon material is used it may be fused to the inflated balloon by the application of heat or other desired bonding technique. Further, an inflation mold may be used to inflate the balloon using heat and pressure so that a desired balloon shape results prior to passing the second balloon material layer. The second balloon material may be cigarette wrapped or helically wrapped.

A yet further embodiment of creating a non-shortening catheter balloon with increased burst pressures is also provided, comprising wrapping a mandrel with a plurality of anisotropic first balloon material layers at a low angle of between 3 and 54 degrees relative to the longitudinal axis to form a balloon preform, these first balloon layers may be oriented in opposing directions relative to the longitudinal balloon axis; exposing the plurality of balloon material layers to heat to bond them together creating a preform; placing the balloon preform in a mold and exposing the balloon preform to internal pressure; inflating the balloon preform as it is continued to be exposed to said internal pressure creating a balloon; and removing the balloon from the mold; and wrapping the inflated balloon with a second balloon material layer at an angle between 54 and 90 degrees to form a high pressure catheter balloon. The second balloon material may be isotropic or anisotropic. The mandrel may be a wire or any other suitable core material to provide a hollow body upon removal from the balloon material. In this method a balloon may be created with the addition of heat and pressure so that no mold is needed. Alternatively, as heat and pressure are added, the balloon may be inflated into a mold.

Additionally, it may be desirable in some shaped balloons to have a catheter shaft comprising a reinforced inner member located adjacent to the longitudinal axis of the balloon and between the shaft and the balloon wherein the reinforced inner member is modulated to compensate for shape shifting or pressure changes in the balloon so as to prevent movement of the catheter balloon upon inflation. The catheter shaft may also comprise an expandable pleated shaft section located adjacent to the longitudinal axis of the balloon wherein the expandable pleated shaft section is formed to compensate for movement or shifting in the balloon upon inflation. To increase the bonding of the seals of the shaped balloon, a catheter shaft comprising an outer seal dimension having both convex portions and concave portions which provide an increased surface area and increased seal strength when attached to the balloon ends.

The following examples are provided to illustrate the present invention. While particular embodiments of the present invention have been illustrated and described herein, the present invention should not be limited to such illustrations and descriptions. It should be apparent that changes and modifications may be incorporated and embodied as part of the present invention within the scope of the following claims and examples.

EXAMPLES

Example 1

The ePTFE membrane used to make the composite film was made in accordance with the teaching in U.S. Pat. No. 5,476,589 to Bacino. Specifically, the ePTFE membrane was longitudinally expanded to a ratio of 55 to 1 and transversely expanded approximately 2.25 to 1, to produce a thin strong membrane with fibrils oriented substantially in the longitudinal direction, and a mass of approximately 3.5 g/m^2 and a thickness of approximately 6.5 micrometers.

The composite film was made by using a saturation coating process whereby a solution of Tecothane TT-1085A polyurethane and tetrahydrofuran (THF) was coated onto the ePTFE membrane using a wire-wound rod coating process. A 3% to 8% by weight solution of Tecothane TT-1085A polyurethane in THF was saturation coated onto the ePTFE membrane to produce a composite film with approximately equal amounts of Tecothane TT-1085A polyurethane on either side of the ePTFE membrane and a total polymer weight application of approximately 50% to 60% of the total final composite film weight.

Example 2

A mechanically balanced composite film was made by using a wire-wound rod coating process whereby a solution of Tecothane TT-1085A polyurethane and tetrahydrofuran (THF) was coated onto an ePTFE membrane. The ePTFE membrane used to make the composite film was made in accordance with the teachings of U.S. patent application Ser. No. 11/334,243. Specifically, the ePTFE membrane was longitudinally expanded to a ratio of 15 to 1 and transversely expanded approximately 28 to 1, to produce a thin strong membrane with a mass of approximately 3.5 g/m$^2$ and a thickness of approximately 8 micrometers. A 3% to 8% by weight solution of Tecothane TT-1085A polyurethane in THF was coated onto the ePTFE membrane to produce a composite film with Tecothane TT-1085A polyurethane on one side of the ePTFE membrane and throughout the ePTFE membrane, and a total polymer weight application of approximately 40% to 60% of the total final composite film weight.

Example 3

A mechanically balanced composite film was made by using a saturation coating process whereby a solution of Tecothane TT-1085A polyurethane and tetrahydrofuran (THF) was coated onto an ePTFE membrane using a wire-wound rod coating process. The ePTFE membrane used to make the composite film was made in accordance with the teachings in Example (2). Specifically, the ePTFE membrane was longitudinally expanded to a ratio of 15 to 1 and transversely expanded approximately 28 to 1, to produce a thin strong membrane with an mass of approximately 3.1 g/m$^2$ and a thickness of approximately 8 micrometers. A 3% to 8% by weight solution of Tecothane TT-1085A polyurethane in THF was saturation coated onto the ePTFE membrane to produce a composite film with approximately equal amounts of Tecothane TT-1085A polyurethane on either side of the ePTFE membrane and a total polymer weight application of approximately 40% to 50% of the total final composite film weight.

Example 4

The composite balloons of the present invention were evaluated on an inflation tester (Interface Associates model PT3070, Laguna Nigel, CA). The inflation tester was filled with distilled, de-ionized water. A balloon was connected to the inflation tester and equilibrated in a water circulation bath (Polyscience Model 210, Niles, IL) at 37 C for 5 minutes. The balloons were cycled three times to 5 atmospheres of pressure at a rate of 6 atmospheres per minute, held at 5 atmospheres of pressure for 10 seconds, and then ramped back down at 6 atmospheres per minute. After cycling the pressure was increased in increments of 1 atmosphere every 10 seconds. The diameter was recorded at each pressure increment with a laser micrometer (Keyence Model LS-7501, Woodcliff Lake, NJ). The length was manually measured with a micrometer (Mitutoyo Absolute Digimatic 500-196, Aurora, IL) several times during the pressure ramp, and the pressure value was recorded for each length measurement taken.

Example 5

The inflatable balloon of the present invention was made by wrapping a composite film of Tecothane TT-1085A polyurethane (Thermedics, Inc, Woburn, MA), and ePTFE membrane, as described in Example 1, over a FEP coated silver plated copper wire (Putnam Plastics LLC, Dayville, CT).

The 0.394 mm diameter wire core was deadsoft copper with silver plating and a 0.2 mm fluorinated ethylene-propylene (FEP) coating.

The composite film was slit to 5 mm wide and wrapped around the wire at a 4 to 5 degree angle from the longitudinal axis of the wire. The wrapped wire was heated for approximately 5 to 30 seconds at 180 C after wrapping. The wire was then wrapped with the composite film in the opposite direction at a 4 to 5 degree angle from the longitudinal axis of the wire and subsequently heated for approximately 5 to 30 seconds at 180 C. The process of wrapping the wire in opposite directions and heating after each pass was repeated until a total of four passes of wrapping was complete. The wrapped wire was wrapped around a pin frame with approximately 30 cm spaces between pins and approximately 180 degrees of wrap around each pin and tied at the ends before being placed into an oven and heated for approximately 30 minutes at 150 C, removed, and permitted to cool to ambient.

Example 6

From the balloon detailed in Example 5, approximately a 2.54 cm section of the composite hollow balloon tube was removed from either end of a longer section of the balloon. The exposed ends of the wire were clamped with hemostats and pulled by hand until the wire had been stretched approximately 5 cm, at which point it was removed from the center of the tube. The plastic FEP coating was removed in a similar fashion, but was stretched approximately 50 cm before it was removed from the balloon.

The hollow balloon was clamped on one side with a hemostat, and Monoject blunt needle with Aluminum luer lock hub (model #8881-202389, Sherwood Medical, St. Louis MO) was inserted approximately 2 cm into the open end of the balloon. The hemostatic valve was tightened to seal the balloon, and was then attached to a Balloon Development Station #210A (Beahm Designs, Inc., Campbell, CA) with nozzle airflow is set to 25-30 units, temperature to 140 C, air pressure to 2.0 atmospheres.

A piece of composite film as described in Example 1 was cut to 22 mm by 47 mm in the longitudinal and transverse directions respectively. The composite film was positioned with the longitudinal axis to run around the circumference of the balloon and the edge running along the length of the balloon was lightly tacked to the balloon by gently touching a Weller EC1002 solder iron (Cooper Industries, Inc. Raleigh, NC) using a Apollo Seiko power source (Model PPM, Apollo Seiko, Inc. Chatsworth, CA). The balloon was then allowed to cool for approximately 10 seconds and the pressure was increased to approximately 4.0 atmospheres. The composite film was then carefully wrapped around the inflated balloon in a cigarette fashion. The section of the composite film that protruded from the ends of the inflated balloon were pressed and twisted gently around the shoulder of the balloon. A second piece of composite film was cut 12 mm by 47 mm in the transverse and longitudinal direction respectively. The composite film was positioned with the transverse axis to run around the circumference of the balloon and the edge running along the length of the balloon was lightly tacked to the balloon as described above. The section of the composite film that protruded from the ends of the inflated balloon were pressed and twisted gently around the shoulder of the balloon.

A 7 mm wide by 50 mm long strip of composite film was wrapped snuggly around either end of the shoulders. The entire balloon was then subjected to the heat zone of the heat box at 140 C for about 1 minute while maintaining approximately 4.0 atmospheres of pressure. Any visual imperfection such as a wrinkle was pressed down by hand from the outside while the balloon was still hot and pressurized from the inside.

Using a Monoject blunt needle with Al Luer Lock Hub (Model 8881-202389, Sherwood Medical, St. Louis, MO), the wrapped balloon was subjected to an internal pressure of approximately 5.4 atmospheres at room temperature for 0.5-2.0 hours, and was subsequently removed from the pressure and cut to size by slicing both uninflated ends to their desired length.

Example 7

A 30.5 cm long section of the composite balloon as described in Example 5 was cut and mounted onto a wrapper consisting of two chuck ends capable of clamping to the ends of the wire and a means for rotating the wire at variable speed. The balanced composite film as described in Example 2 was slit into a 6.35 mm wide strip and six layers were wrapped over the balloon in two locations leaving a 33 mm wide section between the over-wrapped areas. These over-wrapped regions or non-distensible seals were used to terminate the inflated balloon region. The over-wrapped balloon was then heated in a convection oven at 150° C. for 30 minutes unrestrained and subsequently removed from the oven and allowed to cool to room temperature.

The wire and the FEP coating over the wire were removed from the balloon over wire construction. Approximately a 2.54 cm section of the composite hollow balloon tube was removed from either end of a 30.5 cm long section of the balloon. The exposed ends of the wire were clamped with hemostats and pulled by hand until the wire had been stretched approximately 5 cm, at which point it was removed from the center of the tube. The plastic FEP coating was removed in a similar fashion, but was stretched approximately 50 cm before it was removed from the balloon.

The composite hollow balloon was then connected to an Encore 26 inflation device (Boston Scientific Scimed, Maple Grove, MN, Catalog #15-105). The balloon was located in a 2.0 mm diameter polycarbonate mold and pressurized to 10 atmospheres and held at pressure for 5 minutes. The balloon was deflated, removed from the 2.0 mm diameter mold and positioned in a 2.5 mm diameter polycarbonate mold and re-inflated to 10 atmospheres and held for 5 minutes. The process of inflating the balloon in the mold provided a more uniform surface on the balloon.

The composite balloon was then mounted onto a small gauge needle and connected to a rotary union (Dynamic Sealing Technologies, Inc, Ham Lake, MN), and the other end was connected to the rotating end of the wrapper described above. The balloon was inflated through the rotary union using the Encore 26 inflation device to 10 atmospheres with water. The composite film described was slit to approximately 7.6 mm and was used as the second balloon material layer wrapping. The slit composite film was helically wound around the inflated balloon at approximately 75 to 85 degrees relative to the longitudinal axis of the balloon. The process of wrapping the balloon was repeated at the same angle but in the opposite direction.

Using a Weller WSD81 solder gun unit (Cooper Industries, Inc. Raleigh, NC), equipped with a large blunt solder tip set to a 250 set-point, the second balloon material layer wrapping was fused to the first balloon material layer wrapping. The solder tip was pressed lightly against the surface of the balloon while the balloon rotated at 20 rpm, and was slowly traversed along the length of the inflated balloon. The rotation of the balloon was stopped and the solder tip was then pressed lightly against the surface of the inflated balloon and traversed along the length of the balloon at four locations each 90 degrees around the circumference of the balloon. Pressure was relieved and balloon removed from rotary union chucks and trimmed to final length.

This procedure produced a non-shortening wrapped balloon that when inflated to 10 or more atmospheres of pressure created a 3.0 mm diameter and 25 mm long balloon between the non-distensible over-wrapped regions.

Example 8

The core wire and the FEP coating over the core wire were removed from the composite balloon over wire construction described in Example 5.

Approximately a 2.54 cm long section of the composite hollow balloon tube was removed from either end of a 30.5 cm long section of the balloon over wire construction. The exposed ends of the wire were clamped with hemostats and pulled by hand until the wire had been stretched approximately 5 cm, at which point it was removed from the center of the tube. The plastic FEP coating was removed in a similar fashion, but was stretched approximately 50 cm before it was removed from the balloon. A composite hollow balloon tube was produced with a first layer wrapping material at a low (4 to 5 degree) angle of wrap.

A 15.25 cm long section of the composite hollow balloon tube was tied into a knot and clamped with a hemostat on one end. The opposite end was slipped through a Qosina male touhy borst with spin lock fitting (#80343, Qosina Corporation, Edgewood, NY), and a Monoject blunt needle with Aluminum luer lock hub (model #8881-202389, Sherwood Medical, St. Louis MO) was inserted approximately 2.0 cm into the balloon. The hemostatic valve was tightened to seal the balloon, and was then attached to a Balloon Development Station Model 210A (Beahm Designs, Inc., Campbell, CA). The nozzle airflow was set to 25-30 units and the temperature was set to 140 C, air pressure to 2.58 atmospheres. The air pressure was turned on, the center 40 mm long region to be inflated, was subjected to heat for about 2-3 minutes resulting in a balloon with a diameter of 2.85 mm and a length of. The diameter was checked with a Mitutoyo Laser Scan Micrometer Model LSM-3100 (Mitutoyo America Corp, Aurora, IL) while in the inflated state. The resulting balloon had a diameter of 2.85 mm and an inflated length of 27 mm.

Using an Monoject blunt needle with Aluminum luer lock hub (model #8881-202389, Sherwood Medical, St. Louis MO) dispensing needle, the balloon was subjected to an internal pressure of 5.44 atmospheres at room temperature for approximately 1 hour. The Inflation Pressure and length results are shown below.

| Pressure (atm) | 4th Cycle Length (mm) | Diam (mm) |
|---|---|---|
| A | | |
| 1426-49-3G | | |
| 0 | 26.38 | 2.54 |
| 0.07 | 26.15 | 2.53 |
| 1 | 26.15 | 2.89 |
| 2 | 24.75 | 3.04 |
| 2.99 | 24.75 | 3.05 |
| 3.99 | 24.75 | 3.05 |
| 4.98 | 24.75 | 3.04 |
| 5.99 | 24.75 | 3.03 |
| 6.97 | 25.35 | 3.04 |
| 7.97 | 25.35 | 3.08 |
| 8.91 | 24.41 | 3.17 |
| 9.93 | 25.43 | 3.27 |
| 11.01 | 25.76 | 3.42 |
| B | | |
| 1419-101A-2 | | |
| 0 | 30.04 | 1.71 |
| 0.06 | 30.05 | 1.66 |
| 0.99 | 30.3 | 2.14 |
| 1.98 | 30.51 | 2.65 |
| 2.97 | 30.58 | 2.66 |
| 3.97 | 30.58 | 2.67 |
| 4.97 | 30.12 | 2.66 |
| 5.96 | 30.12 | 2.68 |
| 6.97 | 30.12 | 2.72 |
| 7.97 | 29.93 | 2.74 |
| 8.97 | 29.93 | 2.76 |
| 9.96 | 29.75 | 2.78 |
| 10.96 | 29.75 | 2.83 |
| 11.96 | 29.49 | 2.84 |
| 12.95 | 29.32 | 2.88 |
| 13.97 | 29.19 | 2.89 |
| 14.94 | 28.92 | 2.91 |
| 15.96 | 29.92 | 2.93 |
| 16.97 | 29.16 | 2.95 |
| 17.95 | 28.93 | 3 |
| 18.91 | 28.93 | 3.03 |
| 19.93 | 28.93 | 3.05 |
| 20.92 | 28.93 | 3.07 |
| 21.96 | 28.93 | 3.1 |
| 22.92 | 29.02 | 3.18 |
| C | | |
| 1419-102-6B | | |
| 0 | 25.64 | 2.72 |
| 0.06 | 25.57 | 2.72 |
| 0.99 | 25.57 | 2.88 |
| 1.98 | 25.57 | 2.91 |
| 2.97 | 25.57 | 2.91 |
| 3.97 | 25.57 | 2.92 |
| 4.96 | 25.57 | 2.93 |
| 5.97 | 25.57 | 2.95 |
| 6.96 | 25.57 | 2.95 |
| 7.94 | 25.57 | 2.96 |
| 8.95 | 25.69 | 2.97 |
| 9.96 | 26.06 | 2.98 |
| 10.95 | 26.06 | 3 |
| 11.94 | 26.06 | 3.02 |
| 12.93 | 26.06 | 3.02 |
| 13.92 | 26.08 | 3.04 |
| 14.9 | 26.39 | 3.06 |
| 15.89 | 26.4 | 3.1 |
| 16.9 | 26.39 | 3.11 |
| 17.8 | 26.39 | 3.17 |

Example 9

Tensile break load was measured using in INSTRON 1122 tensile test machine equipped with flat-faced grips and a 0.445 kN load cell. The gauge length was 5.08 cm and the cross-head speed was 50.8 cm/min. The sample dimensions were 2.54 cm by 15.24 cm. For longitudinal MTS measurements, the larger dimension of the sample was oriented in the machine, also known as the down-web direction. For the transverse MTS measurements, the larger dimension of the sample was oriented perpendicular to the machine direction, also known as the cross-web direction. Each sample was weighed using a Mettler Toledo Scale Model AG204, then the thickness of the samples was taken using the Kafer FZ1000/30 thickness gauge. The samples were then tested individually on the tensile tester. Three different sections of each sample were measured. The average of the three maximum load (i.e., the peak force) measurements was used. The longitudinal and transverse MTS were calculated using the following equation:

MTS (psi)=(maximum load/cross-section area)*(bulk density(PTFE))/density of the porous membrane), wherein the bulk density of PTFE is taken to be 2.2 g/cc.

What is claimed is:

1. A balloon catheter comprising:
a shaft; and
a balloon coupled to the shaft, the balloon having a longitudinal axis and defining an uninflated length at an uninflated diameter and an inflated length at an inflated diameter,
the balloon comprising a first helical pass of balloon material having been wrapped at a first angle relative to the longitudinal axis when the balloon is at the uninflated diameter and a second helical pass of balloon material having been wrapped at a second angle relative to the longitudinal axis when the balloon is at the uninflated diameter,
the first pass of balloon material then having been bonded to the second pass of material when the balloon is at the inflated diameter, with the first angle and the second angle having each been increased from a lower wrap angle between 3 and 54 degrees at the uninflated diameter to a higher wrap angle between 54 and 90 degrees at the inflated diameter prior to bonding the first pass of balloon material to the second pass of balloon material at the inflated diameter, the first wrap of balloon material having been bonded to the second pass of balloon material at the higher wrap angle such that the inflatable balloon exhibits foreshortening from the uninflated length at the uninflated diameter to the inflated length at the inflated diameter of 10 percent or less.

2. The balloon catheter of claim 1 wherein the balloon exhibits foreshortening of less than 5 percent.

3. The balloon catheter of claim 1 wherein the balloon exhibits foreshortening of less than 2 percent.

4. The balloon catheter of claim 1 wherein the first pass of balloon material and the second pass of balloon material have been annealed at the inflated diameter.

5. The balloon catheter of claim 1 wherein the lower wrap angle is from 3 degrees to 5 degrees.

6. The balloon catheter of claim 1, wherein the lower wrap angle is from 4 degrees to 5 degrees.

7. The balloon catheter of claim 1, wherein the higher wrap angle is 54.7 degrees.

8. The balloon catheter of claim 1, wherein the first pass of balloon material includes an anisotropic material and the second pass of balloon material includes an isotropic material.

9. The balloon catheter of claim 1, wherein the first pass of balloon material includes a porous reinforcing polymer.

10. The balloon catheter of claim 9, wherein the porous reinforcing polymer is expanded PTFE.

11. The balloon catheter of claim 10, wherein the expanded PTFE has a matrix tensile value in one direction of greater than 690 megapascals.

12. The balloon catheter of claim 10, wherein the expanded PTFE has a matrix tensile value in one direction of greater than 960 megapascals.

13. The balloon catheter of claim 10, wherein the expanded PTFE has a matrix tensile value in one direction of greater than 1,200 megapascals.

14. The balloon catheter of claim 1, wherein the balloon has a maximum hoop stress of greater than 400 megapascals.

15. The balloon catheter of claim 1, wherein the balloon has a maximum hoop stress of greater than 600 megapascals.

16. The balloon catheter of claim 1, wherein the first and second angles of the first and second passes of balloon material are equal and opposite on another.

17. The balloon catheter of claim 1, wherein the first pass of balloon material defines a relative angle with the second pass of balloon material, the relative angle between the first and second passes of balloon material defining a hoop stress of the balloon that is twice an axial stress of the balloon when the balloon is inflated to the inflated diameter.

* * * * *